US009592382B2

(12) United States Patent
Kulkarni

(10) Patent No.: US 9,592,382 B2
(45) Date of Patent: Mar. 14, 2017

(54) SYSTEMS AND METHODS FOR RENDERING A CUSTOMIZED ACOUSTIC SCENE FOR USE IN FITTING A COCHLEAR IMPLANT SYSTEM TO A PATIENT

(71) Applicant: ADVANCED BIONICS AG, Staefa (CH)

(72) Inventor: Abhijit Kulkarni, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 70 days.

(21) Appl. No.: 14/761,004

(22) PCT Filed: Jan. 30, 2013

(86) PCT No.: PCT/US2013/023796
§ 371 (c)(1),
(2) Date: Jul. 14, 2015

(87) PCT Pub. No.: WO2014/120146
PCT Pub. Date: Aug. 7, 2014

(65) Prior Publication Data
US 2015/0360029 A1 Dec. 17, 2015

(51) Int. Cl.
*A61N 1/36* (2006.01)
*H04R 25/00* (2006.01)
*A61N 1/372* (2006.01)

(52) U.S. Cl.
CPC ..... *A61N 1/36032* (2013.01); *A61N 1/37247* (2013.01); *H04R 25/70* (2013.01); *A61N 1/37264* (2013.01); *H04R 2225/41* (2013.01); *H04R 2225/67* (2013.01)

(58) Field of Classification Search
CPC . A61N 1/36032; H04R 25/70; H04R 2225/41
See application file for complete search history.

(56) References Cited

U.S. PATENT DOCUMENTS

| 8,027,733 | B1 | 9/2011 | Fridman et al. |
| 8,364,274 | B1 | 1/2013 | Litvak |
| 2012/0029593 | A1 | 2/2012 | Calle et al. |
| 2012/0095528 | A1 | 4/2012 | Miller, III et al. |

FOREIGN PATENT DOCUMENTS

CN            101773696        7/2010

OTHER PUBLICATIONS

First Office Action received in Chinese Patent Application No. 201380071216.0, dated May 25, 2016.
International Search Report and Written Opinion received in International Application No. PCT/US13/023796, dated Jul. 5, 2013.

*Primary Examiner* — Michael Kahelin
(74) *Attorney, Agent, or Firm* — ALG Intellectual Property, LLC

(57) ABSTRACT

An exemplary system includes 1) a fitting facility configured to maintain data representative of a library of one or more sounds and data representative of a library of one or more environments, and 2) a detection facility configured to detect a selection by a user of a sound included in the library of one or more sounds an environment included in the library of one or more environments. The fitting facility is further configured to generate, based on the selected sound and the selected environment, an audio signal representative of an acoustic scene and use the audio signal to fit a cochlear implant system to a patient. Corresponding systems and methods are also disclosed.

20 Claims, 10 Drawing Sheets

502

Source Location (degrees)

| | 0 | 5 | 10 | 15 |
|---|---|---|---|---|
| 10 | $h_1[n]$ | $h_2[n]$ | $h_3[n]$ | $h_4[n]$ |
| 20 | $h_5[n]$ | $h_6[n]$ | $h_7[n]$ | $h_8[n]$ |
| 30 | $h_9[n]$ | $h_{10}[n]$ | $h_{11}[n]$ | $h_{12}[n]$ |
| 40 | $h_{13}[n]$ | $h_{14}[n]$ | $h_{15}[n]$ | $h_{16}[n]$ |

Distance (meters)

Fig. 5

Acoustic Scene Management

Sound — 702

- ☐ AzBio Sentences
- ☒ Male English Speech
- ☐ Female English Speech
- ☐ Male German Speech
- ☐ Female German Speech
- ☐ Music
- ☐ Noise

Source Location — 808

- ☐ 5 degrees
- ☒ 10 degrees
- ☐ 15 degrees
- ☐ 20 degrees

Microphone — 802

- ☐ T-Mic
- ☒ SP Mic
- ☐ Headpiece Mic
- ☐ Beam-Forming Mic

Head Size — 804

- ☒ Adult
- ☐ Pediatric

Distance — 806

- ☐ 10 meters
- ☒ 20 meters
- ☐ 30 meters
- ☐ 40 meters

Environment — 704

- ☒ Classroom
- ☐ Conference Room
- ☐ Church
- ☐ Living Room
- ☐ Office
- ☐ Stadium
- ☐ Busy Restaurant
- ☐ Busy Street
- ☐ Patient-Specific Environment (Cancel)  (Create) — 810

Fig. 8

SYSTEMS AND METHODS FOR RENDERING A CUSTOMIZED ACOUSTIC SCENE FOR USE IN FITTING A COCHLEAR IMPLANT SYSTEM TO A PATIENT

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems have been developed. Cochlear implant systems bypass the hair cells in the cochlea by presenting electrical stimulation directly to stimulation sites (e.g., auditory nerve fibers) by way of one or more channels formed by an array of electrodes implanted in a cochlear implant patient. Direct stimulation of the stimulation sites leads to the perception of sound in the brain and at least partial restoration of hearing function.

When a cochlear implant is initially implanted in a patient, and during follow up visits with a clinician (e.g., an audiologist) thereafter, it is usually necessary to fit the cochlear implant system to the patient. One of the goals of the fitting procedure is to optimize various program parameters (e.g., threshold levels ("T levels"), most comfortable stimulation levels ("M levels"), stimulation rates, input dynamic range ("IDR") values, etc.) to fit the specific needs of the patient. Hence, a typical fitting session involves the psychophysical determination of various program parameters followed by further adjustments during live conversation with the patient in the clinic.

After a full fitting session, it is not uncommon for patients to complain of sub-optimal sound quality and hearing performance when they encounter conditions in the real-world (e.g., restaurants, classrooms, churches, etc.). It is currently impractical for clinics to test patients in these real-world acoustic scenarios. Consequently it is hard to make informed programming changes to ameliorate programming issues without significant amounts of trial and error.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 5 shows an exemplary head-related impulse response set according to principles described herein.

FIG. 8 shows an exemplary graphical user interface according to principles described herein.

DETAILED DESCRIPTION

Figure 1:
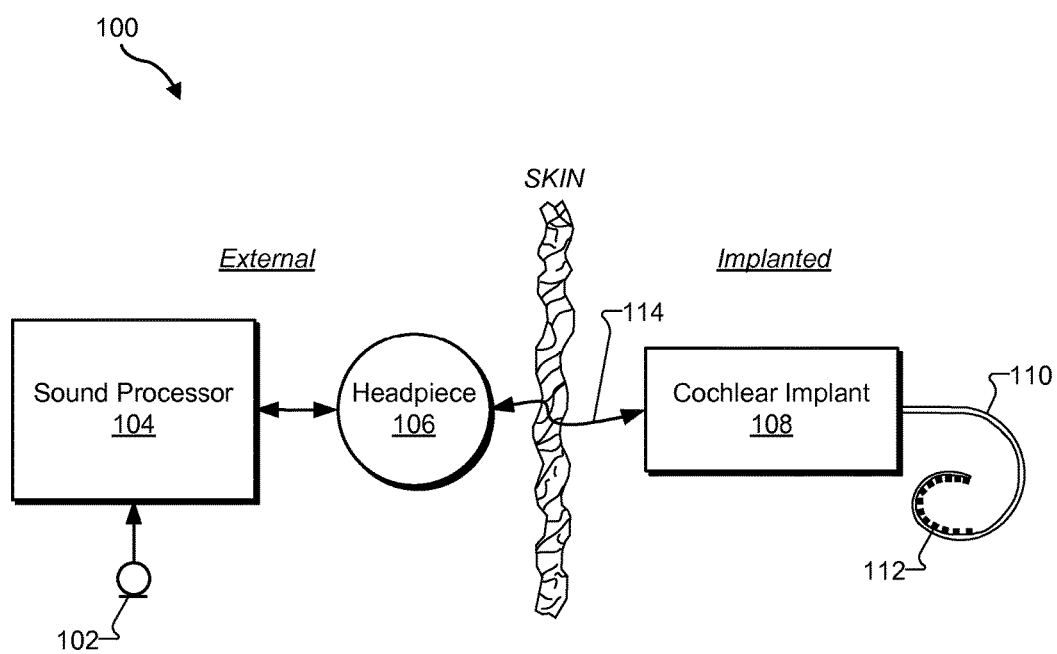
FIG. 1 illustrates an exemplary cochlear implant system according to principles described herein.

Systems and methods for rendering a customized acoustic scene for use in fitting a cochlear implant system to a patient are described herein. As will be described below, a fitting system may 1) maintain data representative of a library of sounds (i.e., a sound library) and data representative of a library of environments (i.e., an environment library), 2) detect a selection by a user of a sound included in the library of sounds and an environment included in the library of environments, 3) generate, based on the selected sound and the selected environment, an audio signal representative of an acoustic scene, and 4) use the audio signal to fit a cochlear implant system to a patient.

Each sound included in the sound library may be representative of acoustic content that may be presented to a cochlear implant patient. For example, the sound library may include music, speech (e.g., speech in a particular language), test sentences (e.g., AzBio sentences), noise, and/or any other acoustic content that may be presented to a cochlear implant patient. Each sound may be generated by a particular sound source (e.g., a person of either gender, one or more musical instruments, etc.) and may be maintained (e.g., stored) by the fitting system in the form of one or more data files (e.g., recorded audio files). Each sound may be "dry" or relatively environment-independent (i.e., each sound may be recorded in an environment (e.g., an anechoic chamber) that minimally affects the quality of the sound).

Each environment included in the library of environments may be representative of a room (e.g., a classroom, a conference room, a living room, an office, etc.), a venue (e.g., a restaurant, a church, a stadium, etc.), an outdoor premises (e.g., a busy street, a worksite, etc.), and/or any other environment in which a cochlear implant patient may be at any given time. In some examples, as will be described below, the library of environments may include one or more patient-specific environments (e.g., a room in the patient's house).

As will be described in more detail below, the systems and methods described herein may allow a user (e.g., a clinician) to selectively combine any sound included in the library of sounds with any environment included in the library of environments in order to create audio signals representative of a variety of different acoustic scenes with negligible overhead in terms of listening rooms or other specialized equipment. These audio signals may then be presented by the fitting system to a patient being fitted with a cochlear implant system in order to ensure optimal operation of the cochlear implant system in a variety of listening conditions.

To illustrate, a clinician may use a fitting system to select a recording of speech generated by a female and an environment representative of a church. The fitting system may accordingly combine the selected speech and environment (e.g., by convolving a sound waveform representative of the speech with a head-related impulse response associated with the selected environment) to render an audio signal representative of an acoustic scene in which the female speaks in the church. The audio signal may then be used to fit a cochlear implant system to a patient (e.g., by presenting the audio signal to the patient, detecting feedback provided by the patient in response to the audio signal, and adjusting one or more program parameters associated with the cochlear implant system based on the feedback).

The clinician may then desire to present to the patient an audio signal representative of a male speaking in the same church. To this end, the clinician may select a recording of speech generated by the male and direct the fitting system to combine the male speech with the same environment representative of the church. The fitting system may accordingly render an audio signal representative of an acoustic scene in which the male speaks in the church. The audio signal may then be used to further fit the cochlear implant system to the patient.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may be additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
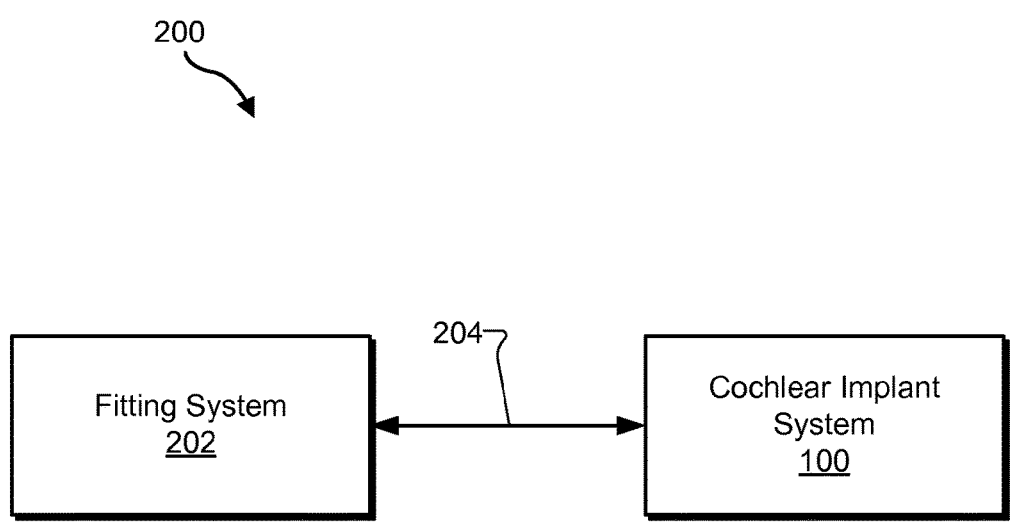
FIG. 2 shows an exemplary configuration in which a fitting system may be selectively and communicatively coupled to a cochlear implant system according to principles described herein.

FIG. 2 shows an exemplary configuration 200 in which a fitting system 202 may be selectively and communicatively coupled to cochlear implant system 100 (e.g., to sound processor 104) by way of a communication link 204. Fitting system 202 and cochlear implant system 100 may communicate using any suitable communication technologies, devices, networks, media, and protocols supportive of data communications.

Fitting system 202 may be configured to perform one or more of the fitting procedures and/or operations described herein. To this end, fitting system 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

Figure 3:
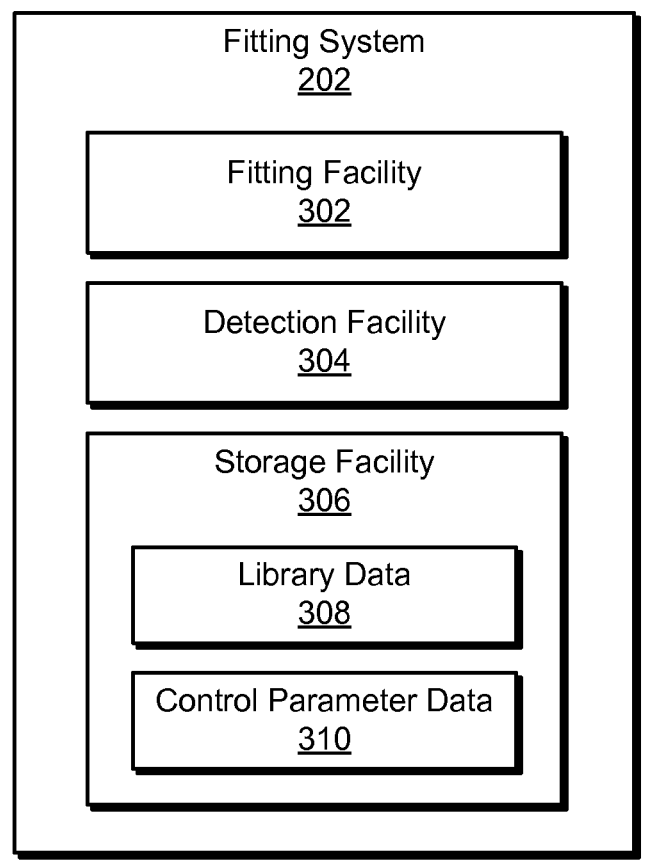
FIG. 3 illustrates exemplary components of a fitting system according to principles described herein.

FIG. 3 illustrates exemplary components of fitting system 202. As shown in FIG. 3, fitting system 202 may include a fitting facility 302, a detection facility 304, and a storage facility 306, which may be communicatively coupled to one another using any suitable communication technologies. Each of these facilities will now be described in more detail.

Storage facility 306 may be configured to store library data 308 (e.g., data representative of or otherwise associated with sounds and environments) and control parameter data 310 (e.g., data representative of control parameters used to fit a cochlear implant system to a patient). It will be recognized that storage facility 306 may maintain additional or alternative data as may serve a particular implementation.

Fitting facility 302 may be configured to perform one or more fitting operations with respect to cochlear implant system 100. For fitting facility 302 may maintain data representative of a library of sounds (i.e., a sound library) and data representative of a library of environments (i.e., an environment library). This may be performed in any suitable manner.

For example, data representative of a sound library may be maintained by maintaining (e.g., storing within storage facility 306) recorded audio files (e.g., MP3, WMA, WAV, DSS, and/or any other type of sound file) representative of each sound. Each recorded audio file may be representative of a sound waveform associated with one of the sounds included in the sound library.

Data representative of an environment library may also be maintained in any suitable manner. For example, data representative of environment library may be maintained in the form of a table of entries each representative of a particular environment.

Figure 4:
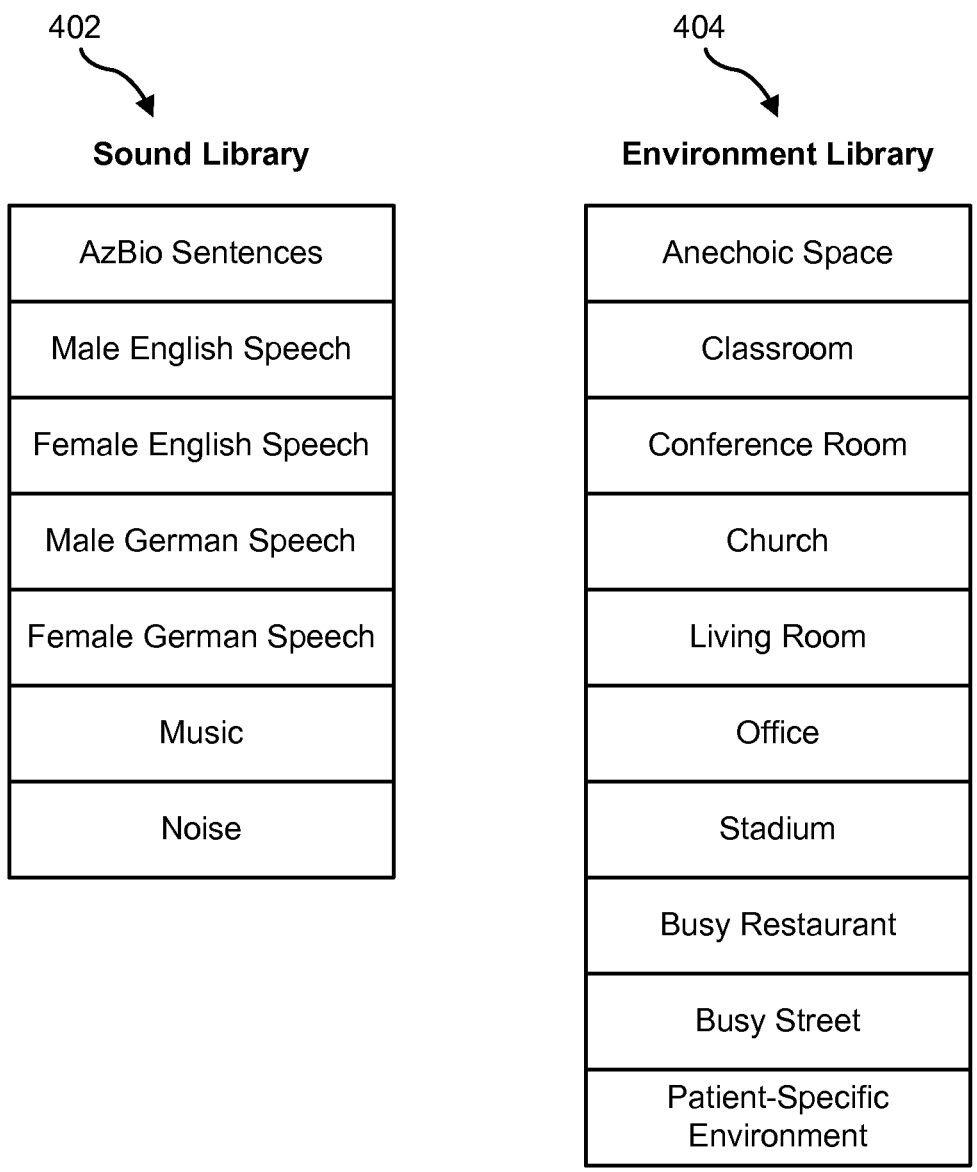
FIG. 4 illustrates an exemplary sound library and an exemplary environment library according to principles described herein.

FIG. 4 illustrates an exemplary sound library 402 and an exemplary environment library 404 that may be maintained by fitting facility 302. As mentioned, sound library 402 may include any type of sound that may be presented to a cochlear implant patient. For example, sound library 402 may include test sentences, speech, music, noise, and/or any other acoustic content that may be presented to a cochlear implant patient. Each sound may be generated by a particular sound source (e.g., a person of either gender, one or more musical instruments, etc.), be in a particular language (e.g., English, German, etc.), and/or have any other suitable characteristic as may serve a particular implementation. To illustrate, sound library 402 includes AzBio sentences, male English speech, female English speech, male German speech, female German speech, music, and noise.

Each environment included in environment library 404 may be representative of a room (e.g., a classroom, a conference room, a living room, an office, etc.), a venue (e.g., a restaurant, a church, a stadium, etc.), an outdoor premises (e.g., a busy street, a worksite, etc.), and/or any other environment in which a cochlear implant patient may be at any given time. In some examples, as indicated in the last entry shown in environment library 404, a patient-specific environment may also be included in environment library 404. The patient-specific environment (e.g., a room in the patient's house) may be provided by providing data representative of a room model associated with the patient-specific environment, as will be described in more detail below.

Fitting facility 302 may be configured to maintain additional data associated with each of the environments included in environment library 404. The additional data, as will be described below, may allow fitting facility 302 to render a variety of different acoustic scenes that may be used to fit a cochlear implant system to a patient.

For example, fitting facility 302 may maintain data representative of one or more head-related impulse responses associated with each environment included in environment library 404. As used herein, a "head-related impulse response" (or "HRIR") may characterize the acoustic path between a sound source and a microphone (e.g., a microphone included in a cochlear implant system) used to detect the sound in a particular environment.

To illustrate, a sound source may be represented by $X(f, \theta)$, where $f$ represents frequency and $\theta$ represents source location (i.e., angle at which sound generated by the sound source arrives at the microphone). Sound produced by the sound source may be recorded by the microphone. The recorded signal may be represented by $Y(f, \theta)$. The acoustic path between the sound source $X(f, \theta)$ and the microphone may be represented by the head-related transfer function $H(f, \theta)$, where $H(f, \theta)=Y(f, \theta)/X(f, \theta)$. In other words, $H(f, \theta)$ embodies the entire transformation of the sound (including the effect of the environment) as it travels from the sound source to the microphone. The head-related transfer function $H(f, \theta)$ may be represented in the time domain as the impulse response associated with the head-related transfer function, as illustrated by $h[n]=IFFT[H(f, \theta)]$, where $h[n]$ represents the head-related impulse response.

As will be described below, an HRIR associated with a particular environment may be used to generate the exact acoustical pressure waveform as it would be received by a microphone included in a cochlear implant system associated with a patient if the patient were actually present in the particular environment. Specifically, the convolution of any sound waveform, $s[n]$, with a head-related impulse response, $h[n]$, associated with a particular environment generates the waveform or signal that would result from the microphone if the microphone were receiving the sound waveform in the particular environment. This is represented by the following equation: $y[n]=s[n]*h[n]$, where $y[n]$ is the audio signal that results from the convolution of $s[n]$ and $h[n]$ and is representative of an acoustic scene in the particular environment. As will be described below, fitting facility 302 may computationally generate $y[n]$ and then use $y[n]$ to fit a cochlear implant system to a patient (e.g., by presenting the audio signal represented by $y[n]$ to the patient).

As noted, an HRIR may be environment-specific (i.e., each environment may have different HRIRs associated therewith). This is because each environment may be unique in the way sound travels and/or reflects of surfaces (e.g., walls) within each environment.

An HRIR may also be microphone-specific (i.e., depend on the particular type and/or position of a microphone used to detect a sound generated by a sound source). For example, a T-mic, a beam-forming microphone, a microphone disposed within a headpiece (e.g., headpiece 106), and a microphone disposed within a sound processor (e.g., sound processor 104) may each have different HRIRs associated therewith with respect to a particular environment.

An HRIR may also be head size-specific (i.e., depend on the head size of the patient associated with a microphone used to detect a sound generated by a sound source). For example, an adult patient and a pediatric patient may have different head sizes and therefore different HRIRs associated therewith.

In addition to each of these factor-specific dependencies, an HRIR may also depend on source location (i.e., an angle at which sound arrives at the microphone from a sound source) and distance (i.e., the distance between the sound source and the microphone). For example, a source location of 0 degrees (i.e., the sound source is directly in front of the microphone) and a source location of 90 degrees (i.e., the sound source is to the side of the microphone) will result in different HRIRs. Similarly, a distance of 10 meters and a distance of 20 meters will result in different HRIRs.

Hence, in some examples, fitting facility 302 may maintain various sets of HRIRs corresponding to each environment. Each set may be microphone and/or head size-specific and may allow fitting facility 302 to create and render a variety of different acoustic scenes that may occur in a particular environment.

To illustrate, FIG. 5 shows an exemplary HRIR set 502 that corresponds to a particular environment and that is specific to a particular type of microphone and/or head size. Similar HRIR sets corresponding to the same environment may be maintained for other types of microphones and head sizes. For example, for a particular environment, fitting facility 302 may maintain a distinct HRIR set for each combination of microphone included in a set of possible microphones and head size included in a set of possible head sizes. To illustrate, if there are five possible types of microphones and two possible head sizes, fitting facility 302 may maintain ten distinct HRIR sets similar to HRIR set 502 for each environment included in environment library 404.

As shown, HRIR set 502 may include a plurality of HRIRs each dependent on a particular source location and a particular distance. For example, the HRIR labeled $h_1[n]$ in FIG. 5 corresponds to a source location of 0 degrees and a distance of 10 meters. As another example, the HRIR labeled $h_{16}[n]$ in FIG. 5 corresponds to a source location of 15 degrees and a distance of 40 meters. It will be recognized that HRIRs corresponding to additional or alternative combinations of source location and distance may be included in HRIR set 502. For example, HRIR set 502 may include HRIRs corresponding to source locations of up to 360 degrees.

Each HRIR included in HRIR set 502 may be generated in any suitable manner. For example, each HRIR may be measured (e.g., by a cochlear implant provider and/or any other entity) prior to the HRIR being loaded into fitting system 202. To illustrate, a cochlear implant provider may set up a microphone within a particular environment (e.g., a church) and use the microphone to record a sound (e.g., an impulse) generated by a sound source at a variety of different source locations within the environment and at a variety of different distances between the sound source and the microphone. This process may be repeated within the same environment with a variety of different microphones and for a variety of different head sizes. HRIRs corresponding to the various sound recordings may then be calculated and stored in the form of one or more data files. The data files may be subsequently loaded onto (e.g., imported) or otherwise accessed by fitting system 202 (e.g., remotely accessed by way of a network).

An HRIR associated with an environment may be further decomposed into an anechoic impulse response and a room model associated with the environment. An anechoic impulse response is a head-related impulse response generated in an anechoic chamber (e.g., a room insulated from exterior sources of noise and designed to completely absorb reflections of sound generated within the room). As will be described below, the anechoic impulse response may be microphone-specific, head size-specific, and source location-specific. A room model associated with an environment may at least model how sound reflects off physical surfaces (e.g., walls) included in the environment. The room model may also model how sound travels in the environment and/or any other characteristic of the environment as may serve a particular implementation.

In some examples, instead of (or in addition to) fitting facility 302 maintaining HRIRs corresponding to each environment included in environment library 404, fitting facility 302 may maintain anechoic impulse responses associated with different microphones and/or head sizes and one or more room models associated with one or more environments included in environment library 404. In this manner, as will be described below, fitting facility 302 may generate an HRIR for any environment represented by a room model, thereby obviating the need for the HRIR to be measured in each actual environment.

Figure 6A:
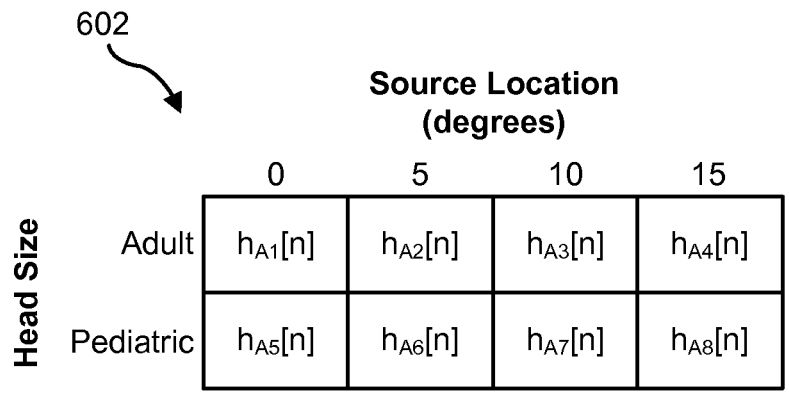
FIG. 6A illustrates an exemplary anechoic impulse response set according to principles described herein.

To illustrate, FIG. 6A illustrates an exemplary anechoic impulse response set 602 that may be maintained by fitting facility 302 and that corresponds to a particular microphone that may be included in a cochlear implant system. Similar sets of anechoic impulse responses may be maintained for other types of microphones that may be included in a cochlear implant system as may serve a particular implementation.

As shown, anechoic impulse response set 602 may include a plurality of anechoic impulse responses (labeled $h_{A1}[n]$ through $h_{A8}[n]$) each dependent on a particular source location and a particular head size. For example, the anechoic impulse response labeled $h_{A1}[n]$ corresponds to a source location of 0 degrees and an adult head size. As another example, the anechoic impulse response labeled $H_{A8}[n]$ corresponds to a source location of 15 degrees and a pediatric head size. It will be recognized that anechoic impulse responses corresponding to additional or alternative combinations of source location and head size may be included in anechoic impulse response set 602. For example, anechoic impulse response set 602 may include anechoic impulse responses corresponding to source locations of up to 360 degrees. It will also be recognized that the anechoic impulse responses are not dependent on distance (i.e., distance between the sound source and the microphone).

Each anechoic impulse response included in anechoic impulse response set 602 may be generated, e.g., by placing the microphone in an anechoic chamber and using the microphone to record an impulse generated by a sound source at a variety of different source locations within the anechoic chamber. This process may be repeated with a variety of different microphones and for a variety of different head sizes. Anechoic impulse responses corresponding to the various sound recordings may then be calculated and stored in the form of one or more data files. The data files may be subsequently loaded onto (e.g., imported) or otherwise accessed by fitting system 202 (e.g., remotely accessed by way of a network).

Figure 6B:
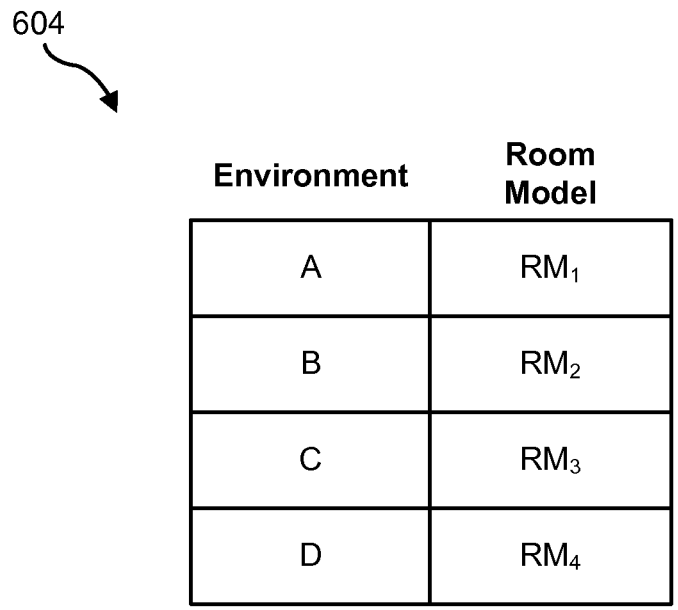
FIG. 6B is a table of room models according to principles described herein.

FIG. 6B is a table 604 of room models (e.g., $RM_1$ through $RM_4$) corresponding to various environments (e.g., environments A through D) that may be maintained by fitting facility 302. As mentioned, each room model may model how sound reflects off physical surfaces (e.g., walls) included in the room model's corresponding environment. The room model may also model how sound travels in the environment and/or any other characteristic of the environment as may serve a particular implementation.

In some examples, fitting facility 302 may generate an HRIR associated with a particular environment based on an anechoic impulse response (e.g., an anechoic impulse response selected from an anechoic impulse response set 502) and a room model associated with the environment (e.g., a room model selected from table 602). This may be performed utilizing any suitable computational heuristic as may serve a particular implementation. The generated HRIR may then be convolved with a sound waveform associated with a sound selected from sound library 402 to render an acoustic scene that may be used to fit a cochlear implant system to a patient.

Returning to FIG. 3, detection facility 304 may detect a selection by a user of a variety of different parameters that may be used to render an acoustic scene. For example, detection facility 304 may detect a selection by a user of a sound included in sound library 402 and an environment included in environment library 404. In response, fitting facility 302 may generate, based on the selected sound and the selected environment, an audio signal representative of an acoustic scene and use the audio signal to fit a cochlear implant system to a patient.

Figure 7:
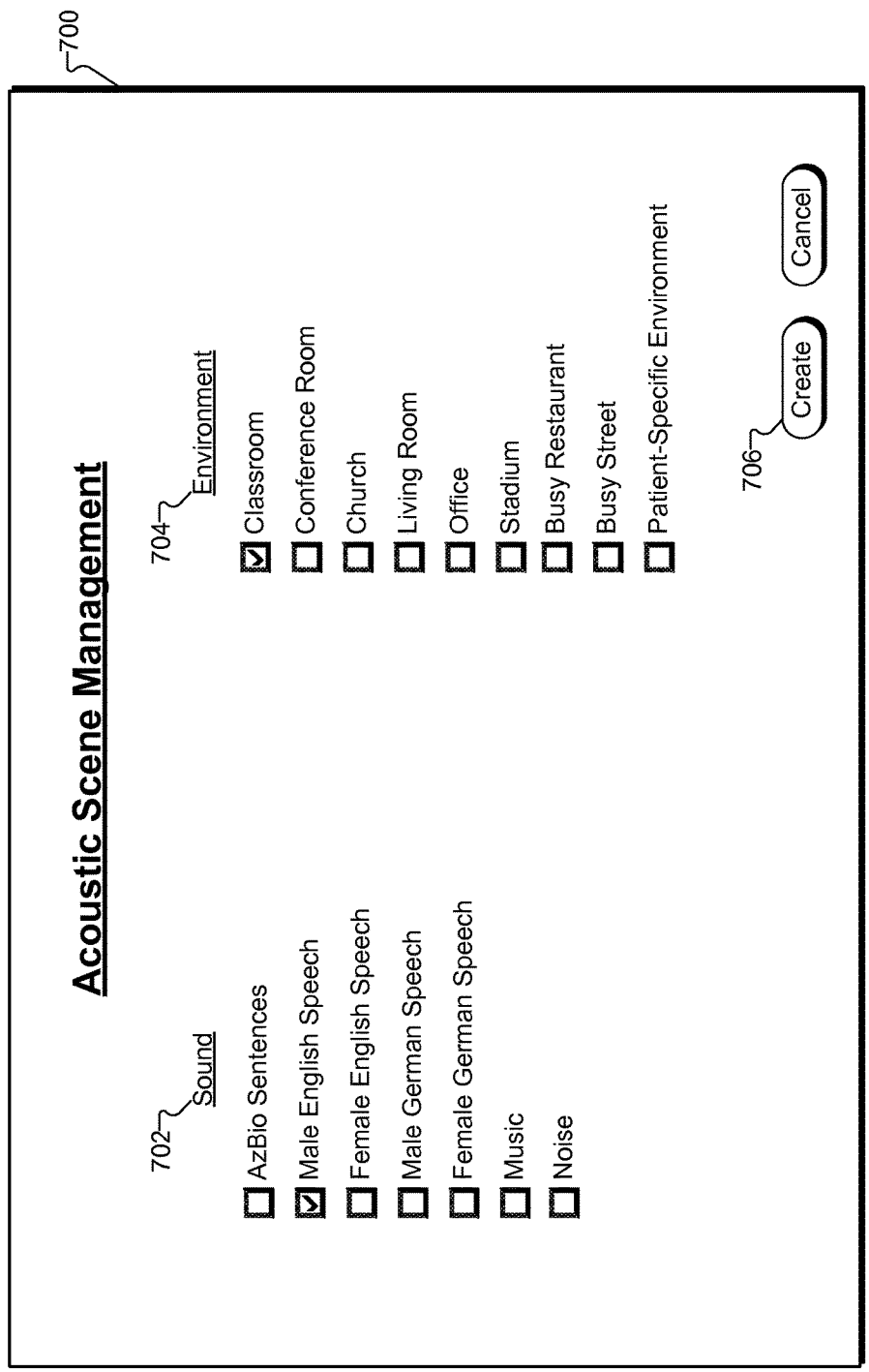
FIG. 7 shows an exemplary graphical user interface according to principles described herein.

To illustrate, FIG. 7 shows an exemplary graphical user interface ("GUI") 700 that may be presented by fitting facility 302 and that may be configured to facilitate user selection of a sound included in sound library 402 and an environment included in environment library 404. GUI 700 may be presented in any suitable manner. For example, fitting facility 302 may present GUI 700 within a display screen associated with fitting system 202.

As shown, GUI 700 may include a list 702 of sounds from which the user may select a desired sound and a list 704 of environments from which the user may select a desired environment. In this particular example, the user may select a particular entry (i.e., a particular sound or environment) included each list by checking a box located next to the particular entry. For example, GUI 700 shows that a user has selected "Male English Speech" as the sound and "Classroom" as the environment.

Once the user has selected a desired sound and environment, the user may select an option 706 to create an audio signal representative of an acoustic scene that is based on the selected sound and environment. For example, in response to a selection of the "Male English Speech" sound and the "Classroom" environment, fitting facility 304 may select or generate an HRIR corresponding to the classroom.

To illustrate, fitting facility 304 may select an already generated HRIR corresponding to the classroom from an HRIR set similar to HRIR set 502. In some examples, the selected HRIR may be associated with a default microphone, a default head size, a default source location, and a default distance. Such default settings may be specified by the user and/or automatically determined by fitting facility 304 (e.g., by analyzing past selections made by the user, detecting a type of microphone actually included in the patient's cochlear implant system, etc.) As will be described below, a user may alternatively specify any one of these parameters.

Once the HRIR has been selected, fitting facility 302 may convolve (or otherwise process) the selected HRIR with a sound waveform representative of the "Male English Speech" sound to generate an audio signal representative of an acoustic scene (i.e., a scene in which the male English speech is spoken in the classroom). The audio signal may then be used to fit a cochlear implant system to the patient. For example, the audio signal may be presented to the patient (e.g., by streaming the audio signal to a sound processor included in the cochlear implant system). Fitting facility 304 may detect (either automatically or based on manual input provided by a clinician or other user) feedback provided by the patient in response to the audio signal and adjust (e.g., automatically or in response to manual input provided by the clinician or other user) one or more control parameters associated with the cochlear implant system (i.e., one or more parameters governing an operation of the cochlear implant system) based on the feedback.

Alternatively, fitting facility 302 may generate the HRIR corresponding to the classroom. For example, fitting facility 302 may maintain data representative of a room model associated with the classroom. Fitting facility 302 may also maintain an anechoic impulse response associated with a microphone included in the cochlear implant system used by the patient. The anechoic impulse response may be selected from an anechoic impulse response set similar to anechoic impulse response set 602 and may correspond to a default head size and a default source location (unless these parameters are selected by the user, as will be described below).

As described above, fitting facility 302 may used the anechoic impulse response and the room model to computationally generate an HRIR corresponding to the classroom. The generated HRIR may then be convolved with the sound waveform representative of the "Male English Speech" sound to generate the audio signal representative of the acoustic scene that is used to fit the cochlear implant system to the patient.

As mentioned, the user may select one or more other parameters in order to further customize the audio signal that is generated by fitting system 202. For example, FIG. 8 shows an exemplary GUI 800 that may be presented by fitting facility 302 and that may be configured to facilitate user selection of a sound included in sound library 402, an environment included in environment library 404, a microphone type, a head size, a distance, and a source location. GUI 800 may be presented in any suitable manner. For example, fitting facility 302 may present GUI 800 within a display screen associated with fitting system 202.

As shown, GUI 800 may include a list 702 of sounds from which the user may select a desired sound, a list 704 of environments from which the user may select a desired environment, a list 802 of microphones from which the user may select a desired microphone, a list 804 of head sizes from which the user may select a desired head size, a list 806 of distances from which the user may select a desired distance, and a list 808 of source locations from which the user may select a desired source location. In this particular example, GUI 800 shows that a user has selected "Male English Speech" as the sound, "Classroom" as the environment, "SP Mic" as the microphone, "adult" as the head size, "20 meters" as the distance, and "10 degrees" as the source location.

Once the user has selected a desired sound, environment, microphone, head size, distance, and source location, the user may select an option 810 to create an audio signal representative of an acoustic scene that is based on the selected parameters.

To illustrate, fitting facility 304 may use the selected parameters to select an already generated HRIR corresponding to the classroom from an HRIR set similar to HRIR set 502. Once the HRIR has been selected, fitting facility 302 may convolve (or otherwise process) the selected HRIR with a sound waveform representative of the "Male English Speech" sound to generate an audio signal representative of an acoustic scene (i.e., a scene in which the male English speech is spoken in the classroom). The audio signal may then be used to fit a cochlear implant system to the patient, as described above.

Alternatively, fitting facility 302 may generate the HRIR corresponding to the classroom. For example, fitting facility 302 may maintain data representative of a room model associated with the classroom. In some examples, the room model may take into account the selected distance. Fitting facility 302 may then select (e.g., from an anechoic impulse response set similar to anechoic impulse response set 602) an anechoic impulse response associated with the selected microphone, head size, and source location and use the anechoic impulse response and the room model to computationally generate an HRIR corresponding to the classroom. The generated HRIR may then be convolved with the sound waveform representative of the "Male English Speech" sound to generate the audio signal representative of the acoustic scene that is used to fit the cochlear implant system to the patient.

It will be recognized that the parameters illustrated in FIG. 8 from which the user may choose are merely exemplary, and that additional or fewer parameters may be selected by a user to generate an audio signal representative of an acoustic scene used to fit a cochlear implant system to a patient.

The modularity of the approaches described above facilitates creation of many different customized acoustic scenes without requiring specialized equipment and logistics. They are language and gender agnostic, thereby allowing sources in any language to be rendered in each environment included in environment library 404.

As another example, a patient-specific environment may be dynamically added to environment library 404 by loading data representative of a room model associated with the patient-specific environment into fitting system 202. To illustrate, detection facility 304 may receive user input representative of a room model associated with an environment (e.g., a room in the patient's house or any other patient-specific environment) not originally included in environment library 404. Fitting facility 302 may then generate, based on the room model and an anechoic impulse response selected in any of the ways described herein, an HRIR associated with the environment. Fitting facility 302 may then generate an audio signal representative of an acoustic scene that may be used to fit the cochlear implant system to the patient by convolving the HRIR with a sound waveform associated with a selected sound, as described above.

In some examples, the systems and methods described herein may be used to fit a cochlear implant system to a bilateral cochlear implant patient (i.e., a patient with cochlear implants implanted in both ears). For example, with respect to a particular environment, fitting facility 302 may maintain or generate a first head-related impulse response that is associated with a first microphone located on a first side of the head of the patient and a second head-related impulse response associated with a second microphone located on a second side (e.g., a side contralateral to the first side) of the head the patient. In response to a user selection of a sound, fitting facility 302 may generate a first audio signal by convolving a sound waveform representative of the sound with the first head-related impulse response. Likewise, in response to the user selection of the sound, fitting facility 302 may generate a second audio signal by convolving the sound waveform representative of the sound with the second head-related impulse response. Fitting facility 302 may then use the first and second audio signals to fit the cochlear implant system to the patient. For example, fitting facility 302 may present the first audio signal to a first ear (e.g., the right ear) of the patient and the second audio signal to a second ear (e.g., the left ear) of the patient.

Additionally or alternatively, the systems and methods described herein may be used to simulate multiple sound sources in a particular environment. For example, it may be desirable to create an acoustic scene in which music is playing at the same time that a person is speaking in a particular environment. To this end, a user may select multiple sounds include in sound library 402 (e.g., by selecting multiple sounds from GUI 700 or GUI 800). In response, fitting facility 302 may convolve an HRIR corresponding to the environment with sound waveforms associated with each selected sound. The resulting signals may be combined (e.g., summed) to generate an audio signal representative of the desired acoustic scene.

To illustrate, the user may select two sounds represented by sound waveforms $s_1[n]$ and $s_2[n]$, respectively. An HRIR corresponding to the environment may be represented by $h[n]$. In this case, fitting facility 302 may generate an audio signal $y[n]$ in accordance with the following equation: $y[n]=s_1[n]*h[n]+s_2[n]*h[n]$. In some alternative examples (e.g., when the sound sources are located at different source locations within the environment), fitting facility 302 may maintain a first HRIR $h_1[n]$ associated with the first sound source and a second HRIR $h_2[n]$ associated with the second sound source. In this case, fitting facility 302 may generate the audio signal $y[n]$ in accordance with the following equation: $y[n]=s_1[n]*h_1[n]+s_2[n]*h_2[n]$.

Figure 9:
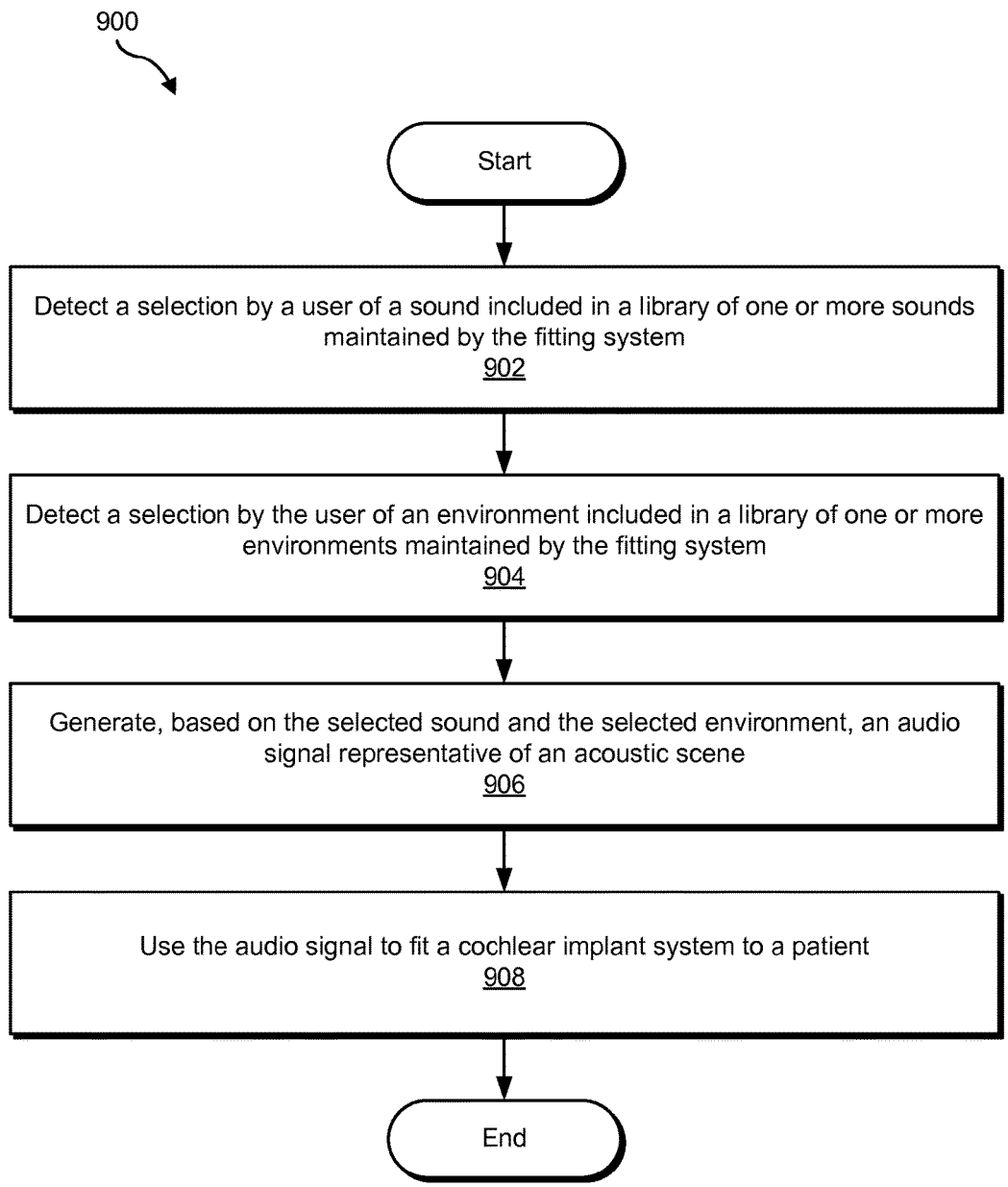
FIG. 9 illustrates an exemplary method of rendering a customized acoustic scene for use in fitting a cochlear implant system to a patient according to principles described herein.

FIG. 9 illustrates an exemplary method 900 of rendering a customized acoustic scene for use in fitting a cochlear implant system to a patient. While FIG. 9 illustrates exemplary steps according to one embodiment, other embodiments may omit, add to, reorder, and/or modify any of the steps shown in FIG. 9. One or more of the steps shown in FIG. 9 may be performed by fitting system 202 and/or any implementation thereof.

In step 902, a fitting system detects a selection by a user of a sound included in a library of one or more sounds maintained by the fitting system. Step 902 may be performed in any of the ways described herein.

In step 904, the fitting system detects a selection by the user of an environment included in a library of one or more environments maintained by the fitting system. Step 904 may be performed in any of the ways described herein. It will be recognized that other parameters may also be selected by a user (e.g., microphone type, source location, distance, and head size).

In step 906, the fitting system generates, based on the selected sound and the selected environment, an audio signal representative of an acoustic scene. Step 906 may be performed in any of the ways described herein.

In step 908, the fitting system uses the audio signal to fit a cochlear implant system to a patient. Step 908 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 10:
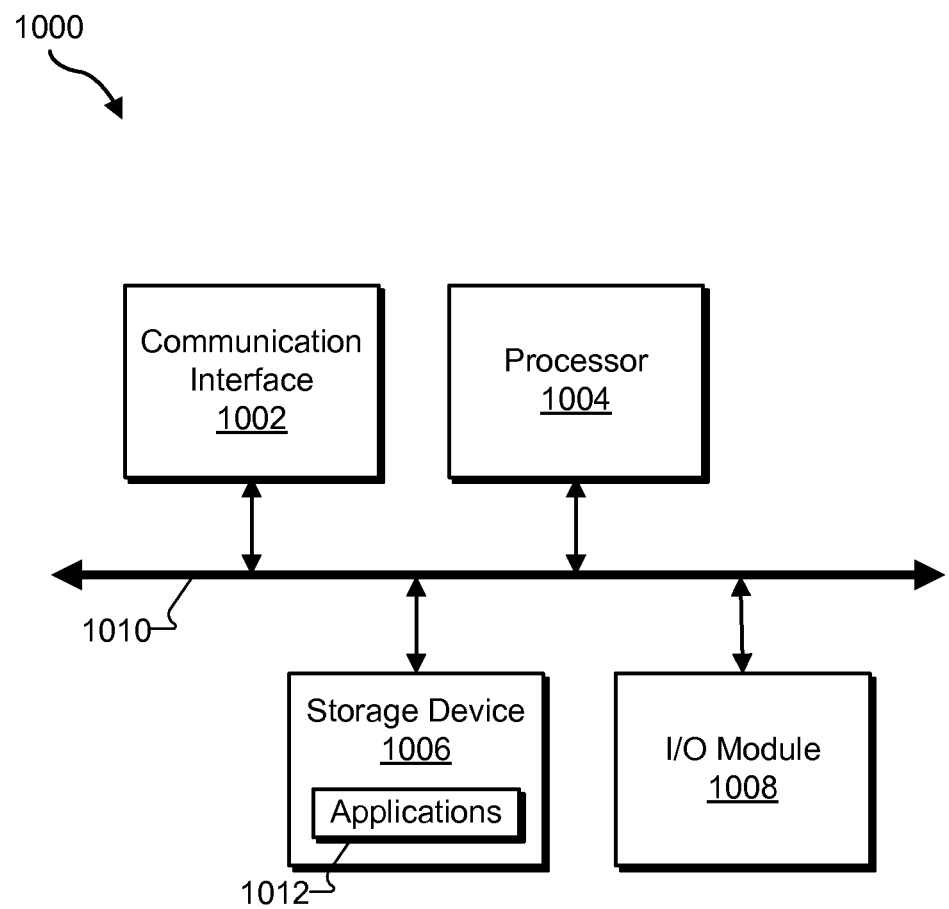
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data or interpreting, executing, and/or directing execution of one or more of the instructions, processes, and/or operations described herein. Processor 1004 may direct execution of operations in accordance with one or more applications 1012 or other computer-executable instructions such as may be stored in storage device 1006 or another computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct processor 1004 to perform one or more processes or functions associated with fitting system 202.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    a fitting facility configured to maintain data representative of a library of one or more sounds and data representative of a library of one or more environments; and
    a detection facility communicatively coupled to the fitting facility and configured to
        detect a selection by a user of a sound included in the library of one or more sounds, and
        detect a selection by the user of an environment included in the library of one or more environments;
    wherein the fitting facility is further configured to
        generate, based on the selected sound and the selected environment, an audio signal representative of an acoustic scene, and
        use the audio signal to fit a cochlear implant system to a patient.

2. The system of claim 1, wherein the fitting facility is further configured to:
    maintain a head-related impulse response associated with the selected environment; and generate the audio signal by convolving a sound waveform representative of the sound with the head-related impulse response.

3. The system of claim 2, wherein the head-related impulse response is further associated with a first microphone located on a first side of the head of the patient, and wherein the fitting facility is further configured to:
maintain an additional head-related impulse response associated with a second microphone located on a second side of the head the patient, the second side being contralateral to the first side;
generate a second audio signal by convolving the sound waveform with the additional head-related impulse response; and
use the second audio signal to further fit the cochlear implant system to the patient.

4. The system of claim 1, wherein the fitting facility is configured to:
use the audio signal to fit the cochlear implant system to the patient by presenting the audio signal to a first ear located on the first side of the head of the patient; and
use the additional audio signal to fit the cochlear implant system to the patient by presenting the additional audio signal to a second ear located on the second side of the head of the patient.

5. The system of claim 1, wherein the fitting facility is further configured to:
maintain an anechoic impulse response associated with a microphone included in the cochlear implant system;
maintain data representative of a room model associated with the selected environment;
generate, based on the anechoic impulse response and the room model, a head-related impulse response associated with the selected environment; and
generate the audio signal by convolving a sound waveform representative of the sound with the head-related impulse response.

6. The system of claim 1, wherein:
the detection facility is further configured to detect a selection by the user of an additional sound included in the library of one or more sounds maintained by the fitting system; and
the fitting facility is further configured to further base the generating of the audio signal on the selected additional sound.

7. The system of claim 6, wherein the fitting facility is configured to generate the audio signal by:
maintaining a head-related impulse response associated with the selected environment;
convolving a sound waveform representative of the sound with the head-related impulse response to generate a first signal;
convolving an additional sound waveform representative of the additional sound with the head-related impulse response to generate a second signal; and
combine the first and second signals to generate the audio signal.

8. The system of claim 6, wherein the fitting facility is further configured to:
maintain an anechoic impulse response associated with a microphone included in the cochlear implant system;
maintain data representative of a room model associated with the selected environment;
generate a head-related impulse response associated with the selected environment based on the anechoic impulse response and the room model; and
generate the audio signal by
convolving a sound waveform representative of the sound with the head-related impulse response to generate a first signal,
convolving an additional sound waveform representative of the additional sound with the head-related impulse response to generate a second signal, and
combining the first and second signals to generate the audio signal.

9. The system of claim 1, wherein:
the detection facility is further configured to
detect a selection by the user of an additional sound included in the library of one or more sounds maintained by the fitting system, and
receive user input representative of a room model associated with an environment not originally included in the library of one or more environments maintained by the fitting facility; and
the fitting facility is further configured to
generate an additional audio signal representative of an additional acoustic scene by
generating a head-related impulse response associated with the environment not originally included in the library of one or more environments maintained by the fitting facility, and
convolving a sound waveform representative of the additional sound with the head-related impulse, and
use the additional audio signal to further fit the cochlear implant system to the patient.

10. The system of claim 9, wherein the fitting facility is configured to generate the head-related response associated with the environment not originally included in the library of one or more environments maintained by the fitting facility by:
maintaining an anechoic impulse response associated with a microphone included in the cochlear implant system; and
computing, based on the anechoic impulse response and the room model, the head-related impulse response associated with the environment not originally included in the library of one or more environments maintained by the fitting facility.

11. The system of claim 1, wherein:
the detection facility is further configured to detect a selection by the user of a microphone included in a library of one or more microphones maintained by the fitting system; and
the fitting facility is configured to further base the generation of the audio signal on the selected microphone.

12. The system of claim 11, wherein the fitting facility is further configured to provide a graphical user interface that allows the user to select at least one of the sound, the environment, and the microphone.

13. The system of claim 1, wherein:
the detection facility is further configured to detect a selection by the user of a source location associated with the selected sound; and
the fitting facility is configured to further base the generation of the audio signal on the selected source location.

14. The system of claim 1, wherein:
the detection facility is further configured to detect a selection by the user of a distance between a source associated with the sound and a microphone included in the cochlear implant system; and
the fitting facility is configured to further base the generation of the audio signal on the selected distance.

15. The system of claim 1, wherein:
the detection facility is further configured to detect a selection by the user of a head size; and
the fitting facility is configured to further base the generation of the audio signal on the selected head size.

16. The system of claim 1, wherein the fitting facility is configured to use the audio signal to fit the cochlear implant system to the patient by:
presenting the audio signal to the patient;
detecting feedback provided by the patient in response to the audio signal; and
adjusting one or more control parameters associated with the cochlear implant system based on the feedback.

17. A fitting system comprising:
a fitting facility configured to maintain data representative of a plurality of sound waveforms representative of a plurality of sounds, data representative of a plurality of anechoic impulse responses each associated with a distinct microphone included in a plurality of microphones, and data representative of a plurality of room models each associated with a distinct environment included in a plurality of environments;
a detection facility communicatively coupled to the fitting facility and configured to detect a selection by a user of a sound included in the plurality of sounds, a microphone included in the plurality of microphones, and an environment included in the plurality of environments;
wherein the fitting facility is further configured to
generate, based on an anechoic impulse response associated with the selected microphone and included in the library of anechoic impulse responses and a room model associated with the selected environment and included in the library of room models, a head-related impulse response associated with the selected microphone and the selected environment,
generate an audio signal representative of an acoustic scene by convolving a sound waveform included in the plurality of sound waveforms and representative of the selected sound with the head-related impulse response, and
use the audio signal to fit a cochlear implant system to a patient.

18. The system of claim 17, wherein:
the detection facility is further configured to detect a selection by the user of a source location associated with the selected sound; and
the fitting facility is configured to further base the generation of the audio signal on the selected source location.

19. The system of claim 17, wherein:
the detection facility is further configured to detect a selection by the user of a head size; and
the fitting facility is configured to further base the generation of the audio signal on the selected head size.

20. A method comprising:
detecting, by a fitting system, a selection by a user of a sound included in a library of one or more sounds maintained by the fitting system;
detecting, by the fitting system, a selection by the user of an environment included in a library of one or more environments maintained by the fitting system;
generating, by the fitting system based on the selected sound and the selected environment, an audio signal representative of an acoustic scene; and
using, by the fitting system, the audio signal to fit a cochlear implant system to a patient.

* * * * *